(12) United States Patent
Kaufman et al.

(10) Patent No.: US 10,660,785 B2
(45) Date of Patent: May 26, 2020

(54) LONG DURATION WASTE MANAGEMENT SYSTEM

(71) Applicant: Hamilton Sundstrand Corporation, Charlotte, NC (US)

(72) Inventors: Cory Kaufman, Webster, TX (US); David Autrey, Houston, TX (US); Gary Van Stephenson, Houston, TX (US); Shawn R. Macleod, Pearland, TX (US)

(73) Assignee: HAMILTON SUNDSTRAND CORPORATION, Charlotte, NC (US)

( * ) Notice: Subject to any disclaimer, the term of this patent is extended or adjusted under 35 U.S.C. 154(b) by 575 days.

(21) Appl. No.: 15/476,065

(22) Filed: Mar. 31, 2017

(65) Prior Publication Data

US 2018/0280189 A1 Oct. 4, 2018

(51) Int. Cl.
*A61F 5/451* (2006.01)
*A61F 5/44* (2006.01)
*A61F 5/441* (2006.01)
*B64G 6/00* (2006.01)
*A61F 5/442* (2006.01)

(52) U.S. Cl.
CPC .......... *A61F 5/4408* (2013.01); *A61F 5/4401* (2013.01); *A61F 5/441* (2013.01); *A61F 5/442* (2013.01); *A61F 5/4404* (2013.01); *A61F 5/4405* (2013.01); *A61F 5/451* (2013.01); *B64G 6/00* (2013.01)

(58) Field of Classification Search
CPC .... A61F 5/4401; A61F 5/4404; A61F 5/4405; A61F 5/4408; A61F 5/441; A61F 5/442; A61F 5/451; B64G 6/00
See application file for complete search history.

(56) References Cited

U.S. PATENT DOCUMENTS

| | | | |
|---|---|---|---|
| 3,804,093 A * | 4/1974 | Fell | A61F 5/448 604/355 |
| 4,031,897 A * | 6/1977 | Graetz | A61F 5/4401 604/347 |
| 5,334,174 A | 8/1994 | Street | |
| 6,554,817 B1 | 4/2003 | Oki et al. | |
| 6,920,646 B2 | 7/2005 | Crye et al. | |
| 8,569,568 B2 | 10/2013 | Roe et al. | |
| 8,690,846 B2 | 4/2014 | Chen et al. | |
| 2008/0091153 A1 | 4/2008 | Harvie | |

* cited by examiner

*Primary Examiner* — Kai H Weng
(74) *Attorney, Agent, or Firm* — Carlson, Gaskey & Olds, P.C.

(57) ABSTRACT

A garment for long duration waste removal includes, among other things, a containment layer, a containment interface defining a passage, a storage container extending from the containment interface, and a cleansing member routed through the passage, and into the storage container. The cleansing member is moveable relative to the containment layer to remove solid waste. A waste management system for long duration vehicle operations is also disclosed.

6 Claims, 8 Drawing Sheets

LONG DURATION WASTE MANAGEMENT SYSTEM

BACKGROUND

This disclosure relates to a waste management system, and more particularly to a garment that can be worn for a prolonged duration.

During space missions, astronauts may conduct operations inside a pressurized suit in a low gravity environment. Contingency mission conditions, which may be caused by depressurization of a space vehicle, may require astronauts to remain in the pressurized suits for a relatively long period of time, such as several hours or days. Astronauts may be unable to utilize onboard waste management systems during such missions. Astronauts are typically provided with absorbent diapers for the collection of urine and fecal matter, which are worn underneath thermal garments and may be difficult to replace during contingency mission conditions.

SUMMARY

A garment for waste removal according to an exemplary aspect of the present disclosure includes, among other things, a body side layer having a construct that allows passage of liquid waste, but obstructs passage of solid waste, the body side layer defining a first opening. A first, substantially impermeable containment layer extends along the body side layer, the first containment layer defining a second opening. An elongated cleansing member has a first end routed through the first and second openings. The cleansing member translatable along the body side layer to remove solid waste.

A garment for waste removal according to an exemplary aspect of the present disclosure includes, among other things, a first, substantially impermeable containment layer, an elongated cleansing member, and a containment interface defining a passage, the elongated cleansing member translatable through the passage to remove solid waste.

A waste management system for long duration vehicle operations according to an exemplary aspect of the present disclosure includes, among other things, a garment comprising a first, substantially impermeable containment layer, a containment interface defining a passage, a storage container extending from the containment interface, and a cleansing member routed through the passage, and into the storage container. The cleansing member is moveable relative to the first containment layer to remove solid waste. An actuation assembly is moveable to draw a portion of the cleansing member into the storage container in response to activation of a control mounted to a protective suit.

The various features and advantages of disclosed embodiments will become apparent to those skilled in the art from the following detailed description. The drawings that accompany the detailed description can be briefly described as follows.

DETAILED DESCRIPTION

Figure 1:
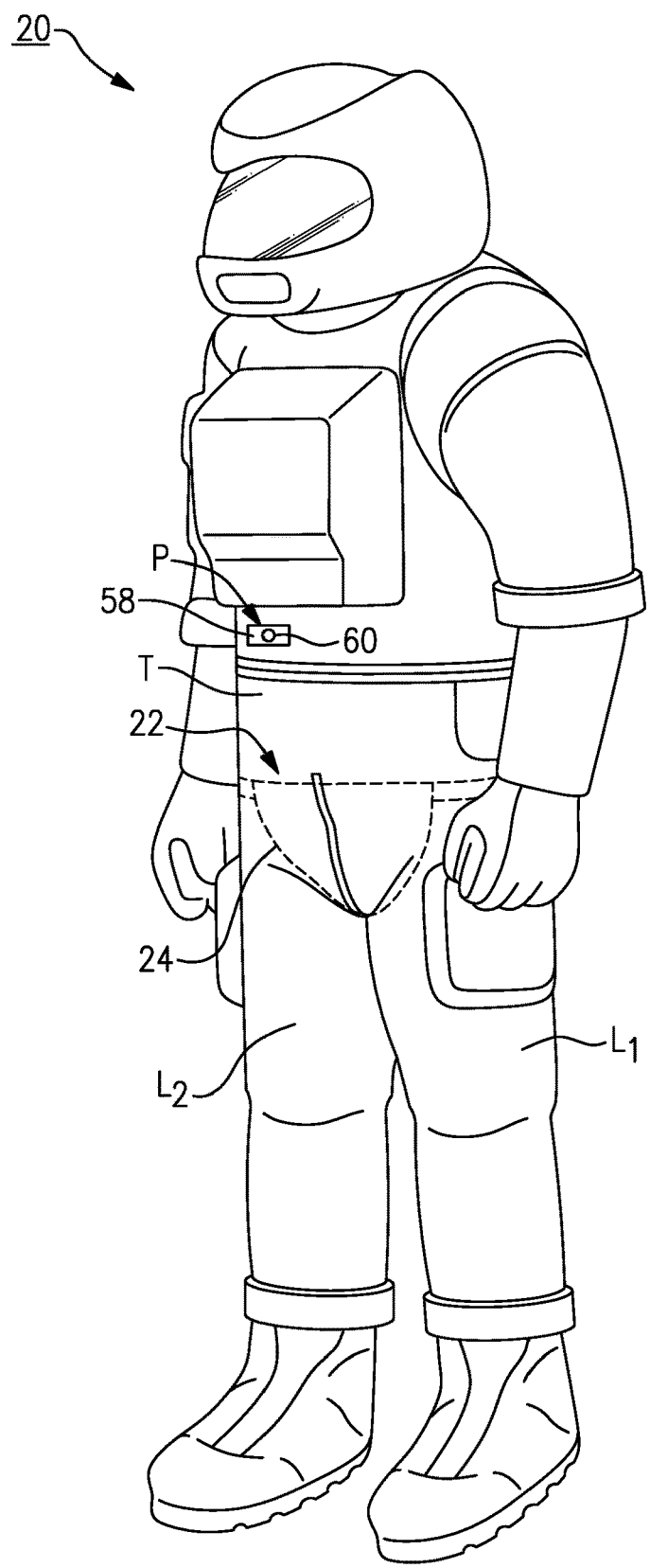
FIG. 1 is a schematic view of a protective suit.

FIG. 1 illustrates a protective suit 20 that can be pressurized and may be utilized for long duration, low gravity space operations. These operations may require that an operator or person wear the protective suit 20 for a period of multiple hours or days without unsealing or depressurizing the protective suit 20. A person wearing the protective suit 20 can be provided with a waste removal or management system 22 for removing both liquid and solid waste discharged by the person. The waste management system 22 includes a garment 24 contoured for abutment with a person, such as torso T and legs L1, L2 of the person, for example. The garment 24 can be worn underneath, or attached to, a thermal layer or liquid cooling garment internal to the protective suit 20. In this disclosure, like reference numerals designate like elements where appropriate and reference numerals with the addition of one-hundred or multiples thereof designate modified elements that are understood to incorporate the same features and benefits of the corresponding original elements. Although this disclosure primarily discusses space operations in protective suit 20, other systems and missions may benefits from the teachings herein, including long duration flights.

Figure 2:
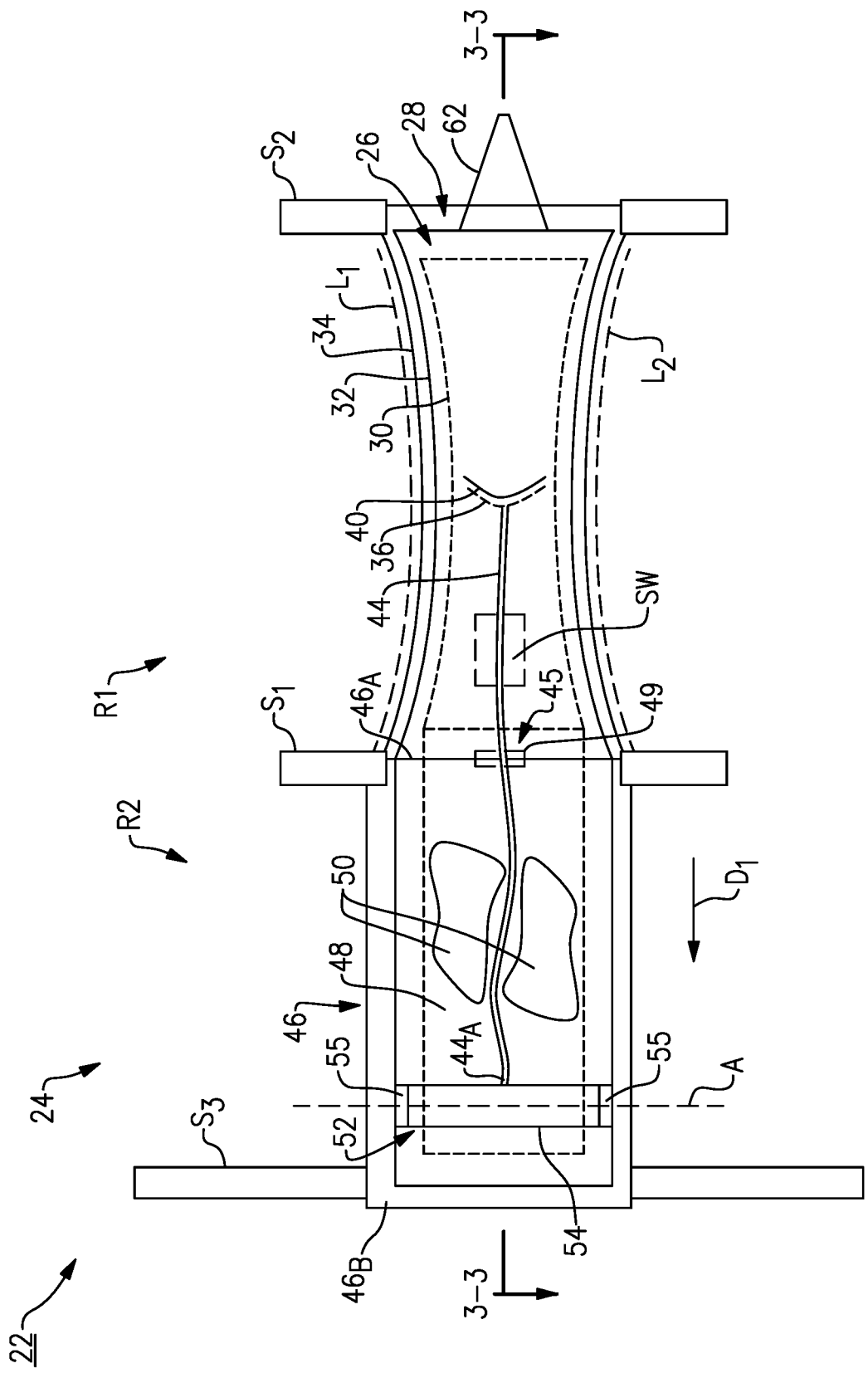
FIG. 2 is a plan view of a waste management system.

Referring to FIG. 2, the garment 24 includes a first region R1 for containing liquid and solid waste and a second region R2 for storing solid waste deposited in the first region R1. The first region R1 is situated between legs L1, L2 when worn by the person. The second region R2 can be secured to a mid-back or torso T of the person with straps or other means. For example, straps S1, S2 can cooperate to secure the first region R1 around the lower waste or torso T, and straps S3 can be secured around the mid-back or a relatively higher portion of the torso T to support the second region R2 of the garment 24. The straps S1, S2, S3 can be Velcro, elastic, or adjustable webbing, for example. In alternative examples, the first region R1 can be secured to another portion of the person, such as one of legs L1, L2 or an abdomen region of the torso T and/or the second region R2 can be located in another region of the protective suit 20 like down either leg L1 or L2. In some examples, the straps S1, S2, S3 are omitted, and ends of the first region R1 are coupled to each other to provide a slip-on function.

Figure 3:
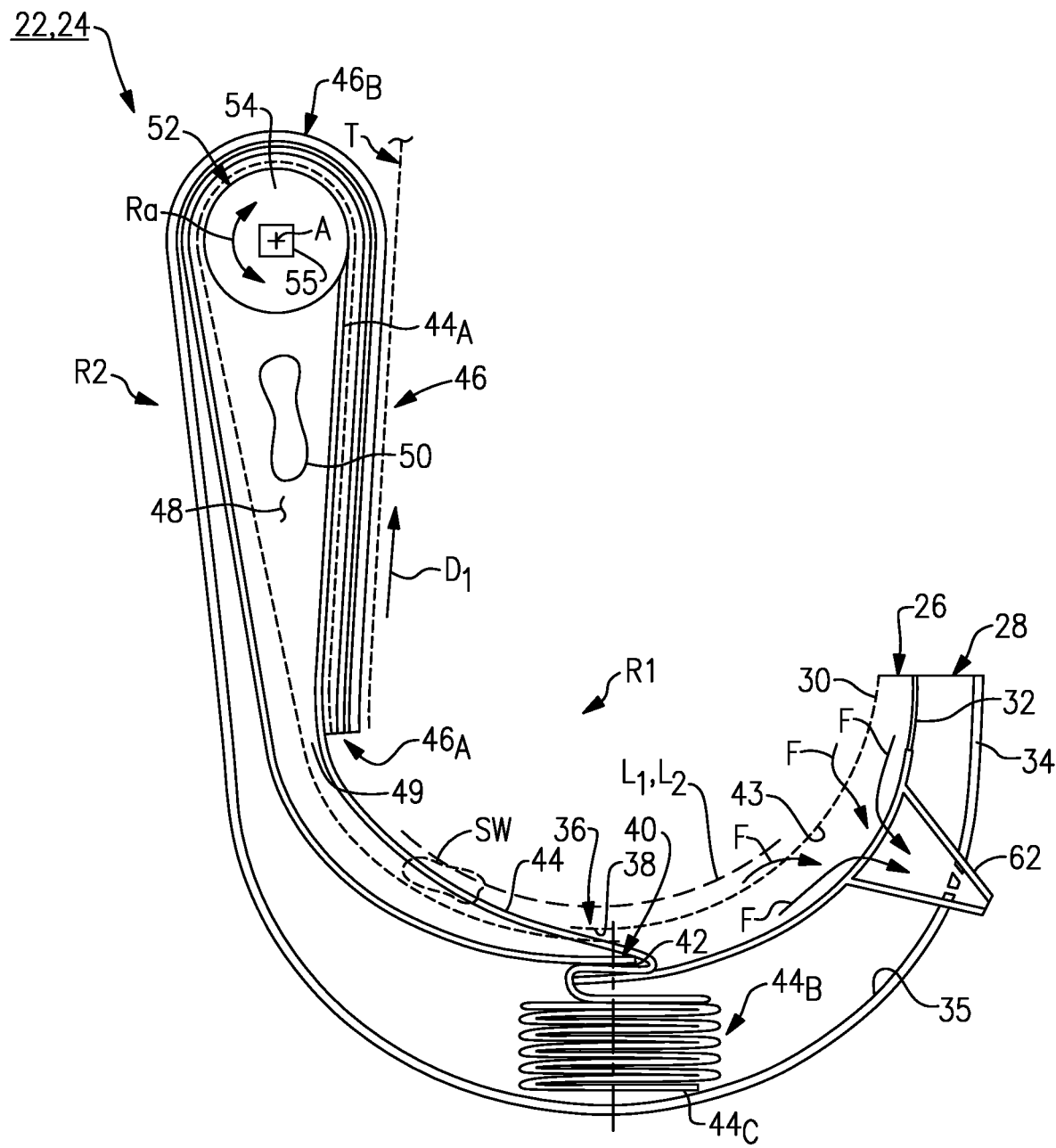
FIG. 3 is a sectional view of the waste management system of FIG. 2 along reference line 3-3.

Referring to FIG. 3 with continued reference to FIG. 2, the garment 24 includes a first containment track 26 and a second containment track 28 comprising multiple layers of material. The first containment track 26 can provide a primary layer of protection or containment of fluid F and solid waste SW that may otherwise escape into the protective suit 20. The second containment track 28 can provide a redundant layer of containment with respect to fluid F and solid waste SW.

The first containment track 26 is defined by a body side layer 30 (shown in dashed lines) and a first containment layer 32. The body side layer 30 and the first containment layer 32 define a first or inner cavity 43 for collection of fluid F discharged by the person. The second containment track 28 is defined by the first containment layer 32 and a second containment layer 34. The body side layer 30 is configured for direct abutment with the person. The first containment layer 32 is situated between the body side layer 30 and the second containment layer 34. In alternative examples, one of the first containment layer 32 or the second containment layer 34 is omitted.

The body side layer 30 has a construct that allows passage of urine or other fluid F, but filters or substantially obstructs passage of feces or other solid waste SW. The body side layer 30 can be made of a relatively porous material. In one example, the body side layer 30 includes a coarse mesh fabric weave made of strands of non-biodegradable materials such as polymers. In another example, the body side layer 30 is made of weave of organic fibers. Suction can be provided to assist in migration of fluid F through the body side layer 30 and into the inner cavity 43. The first containment layer 32 and the second containment layer 34 can be hydrophobic or substantially impermeable to liquid. A perimeter of the first containment layer 32 is sealed or otherwise joined with a perimeter of the second containment layer 34. A perimeter of the body side layer 30 is sealed or otherwise joined with a perimeter of the first containment layer 32. The body side layer 30, first containment layer 32 and the second containment layer 34 can be adhered to each other utilizing an epoxy, for example, or heat sealed together depending on their respective materials.

The body side layer 30 has a first flap 36, which defines a first or inner opening 38. The first containment layer 32 has a second flap 40 which defines a second or outer opening 42. The flaps 36, 40 can be located at the rearward two-thirds of the first region R1, such as between the genitalia and anus of the person when the garment 24 is worn, for example. The garment 24 can be unisex, or can be dimensioned for the male or female anatomy. The flaps 36, 40 are spaced apart from sides of the first containment track 26 and the second containment track 28. In the illustrated example, the first flap 36 is substantially aligned with the second flap 40 to function as a double fold, with the inner opening 38 offset from the outer opening 42 to provide a generally serpentine path. The serpentine arrangement reduces a likelihood of fluid F escaping from the first containment track 26 into the second containment track 28.

The garment 24 includes an elongated cleansing member 44 for removal of solid waste SW from the first region R1. The second containment layer 34 extends along the first containment layer 32 to define a second or outer cavity 35 for receiving a length 44B of the cleansing member 44. In alternative examples, the length 44B of the cleansing member 44 is received in the inner cavity 43.

The cleansing member 44 can be made of a biodegradable or absorbent material such as cloth. The cleansing member 44 can be at least partially saturated or impregnated with a biocompatible disinfectant, cleansing solution and/or deodorizer. The cleansing member 44 can also have a smooth texture to improve comfort, and/or a fibrous texture to improve adhesion to solid waste SW, for example. The cleansing member 44 can be flexible and conform to the body, and can be dimensioned for contact with or near the anus.

The cleansing member 44 has a first end 44A routed from outer cavity 35, through the outer opening 42 and the inner opening 38, and into the storage container 46. The flaps 36, 40 can have an elastic material for conforming the openings 38, 42 about a perimeter of the cleansing member 44, thereby reducing passage of fluid F therethrough.

The length 44B and a second end 44C of the cleansing member 44 are received in the outer cavity 35 of the second containment track 28. The length 44B of the cleansing member 44 can be folded in a zigzag pattern and placed in the outer cavity 35, which allows for continuous pulling of the cleansing member 44 with reduced bunching and providing for a relatively compact arrangement. In other examples, the length 44B is spooled onto a carrier. The cleansing member 44 can absorb fluid F that escapes through outer opening 42 into the second containment track 28 through a capillary or wicking action.

The cleansing member 44 is translatable or otherwise moveable along a surface of the body side layer 30 to adhere to, or otherwise remove, solid waste SW near the anus. Since the cleansing member 44 is translatable along, and relative to, the body side layer 30 and the first containment layer 32, different portions of the length 44B of the cleansing member 44 can be utilized to remove solid waste SW over an extended period of time while the garment 24 is worn by the person. This can improve comfort and cleanliness of the person during long duration operations in the protective suit 20. Further translation of the cleansing member 44 can provide a wiping or cleansing action to sanitize the skin.

The storage container 46 extends from the first containment layer 32 and the second containment layer 34 at a containment interface 45. The storage container 46 can be elevated relative to the first containment track 26 and the second containment track 28 when worn by the person, as illustrated by FIG. 3. The storage container 46 can have a generally rectangular or elliptical geometry, and can maintain a close profile to the user, for example.

The containment interface 45 defines an opening or waste passage 49 (shown in dashed lines in FIG. 2) between regions R1, R2 for providing access to a storage cavity 48 defined by the storage container 46. The first end 44A of the cleansing member 44 passes through the waste passage 49 and is received in the storage cavity 48. One or more desiccant packs 50 can be situated in the storage cavity 48 for absorbing moisture collected therein and for reducing bacterial activity and odors. Desiccants can absorb moisture to limit bacterial growth, which over a duration of time increases sanitation and decreases odor as compared to a system without a desiccant.

The first containment layer 32 and the second containment layer 34 extend from the first region R1 and are folded on top of themselves to define walls of the storage container 46, with the storage container 46 being substantially flexible. The body side layer 30 can also extend into the storage cavity 48. In alternative examples, the storage container 46 is a separate component detachable from the first region R1 and can be constructed of multiple layers of substantially impermeable materials including those disclosed herein.

Figure 4:
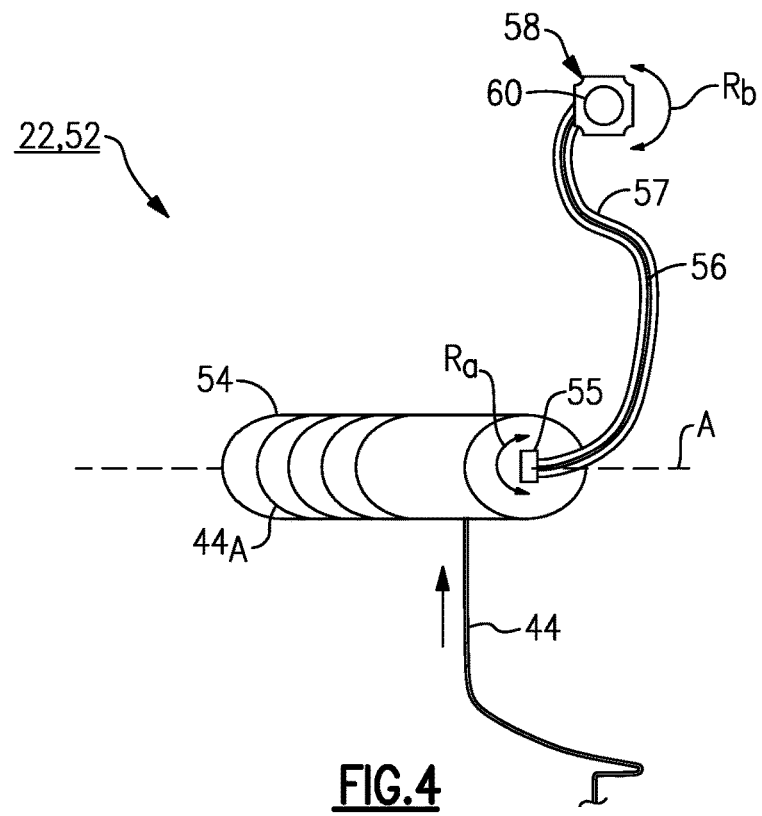
FIG. 4 illustrates an actuation assembly for the waste management system of FIG. 2.

Referring to FIG. 4 with continued reference to FIGS. 2 and 3, the waste management system 22 can include an actuation assembly 52. The actuation assembly 52 is coupled to the first end 44A of the cleansing member 44 and is moveable to draw a portion of the cleansing member 44 into the storage cavity 48. The actuation assembly 52 includes an elongated, rotatable spool 54 mechanically attached or otherwise coupled to a flexible torsion cable 56 at axis A. At least a portion of the spool 54 is located in the storage cavity 48 and is rotationally coupled to support means 55 attached to walls at end 46B of the storage container 46. The support means 55 can be provided with one or more seals to inhibit flow of fluid from the storage cavity 48. The spool 54 is rotatable about axis A in direction Ra in response to rotation of the torsion cable 56, which causes the cleansing member 44 to be wound around a circumference of the spool 54. The torsion cable 56 can be provided with a relatively rigid sheath or jacket 57 to reduce frictional contact with the person and twisting of the torsion cable 56 when under torsion. In alternative examples, cable 56 is a flexible cable wound around the spool 54 to impart rotation.

The waste management system 22 can include a control 58 for selectively activating the actuation assembly 52 to cause a portion of the cleansing member 44 to be drawn into the storage cavity 48. The control 58 can be mounted to and integrated at a port P of the protective suit 20 (FIG. 1). The control 58 can include a rotatable knob 60 or another device for actuating the torsion cable 56, which can be located external to the protective suit 20 for ease of access. The knob 60 is mechanically attached to the torsion cable 56 such that rotation of the knob 60 in direction Rb causes rotation of the torsion cable 56, which imparts rotation of the spool 54 in direction Ra. The knob 60 can include a gear reduction to reduce the number of revolutions for translating the cleansing member 44, or a ratcheting feature to limit backwards rotation of the knob 60. In alternative examples, the control 58 includes an electric motor operatively coupled to an electrical switch, with the motor powered by a battery pack or other power supply. The switch can be placed at a location under a bladder of the protective suit 20 or can be remotely activated, for example.

Figure 5:
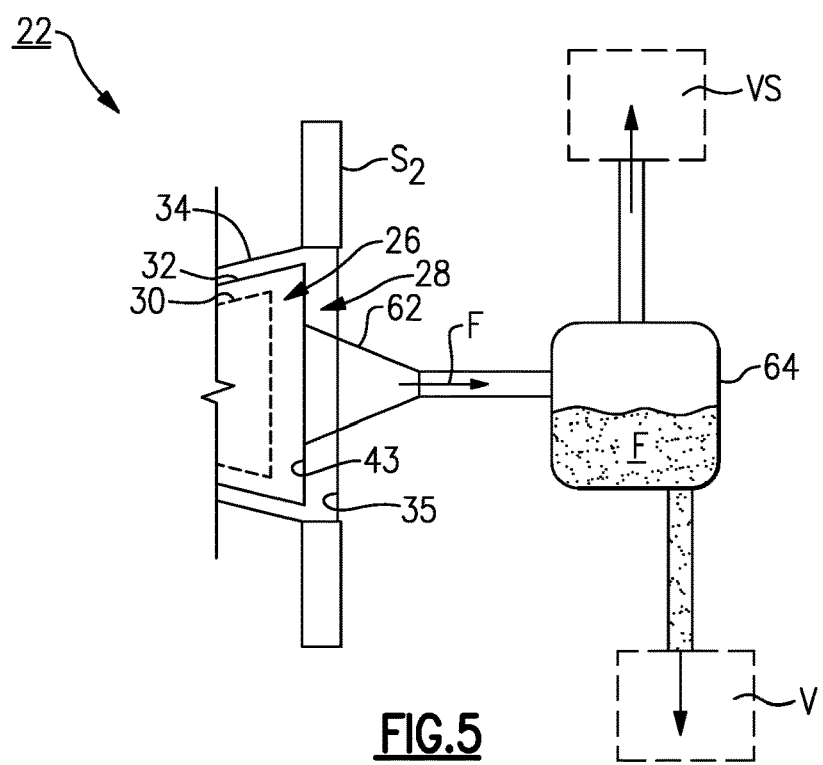
FIG. 5 illustrates a liquid separator for the waste management system of FIG. 2.

Referring to FIG. 5 with continued reference to FIGS. 2 and 3, the waste management system 22 can include a conduit or capture funnel 62 coupled to the first containment track 26. The capture funnel 62 can be flexible and tapers inward from the first containment track 26 to accelerate the flow of fluid F from the inner cavity 43. In other examples, the capture funnel 62 has a generally uniform diameter along its length. The capture funnel 62 can mate with a liquid separator 64 that interconnects the capture funnel 62 and a vacuum source VS. The liquid separator 64 can vent fluid F to a vent V. The vent V may discharge fluid F overboard or collect the fluid F at a remote location. This can allow the fluid F to be recycled for later utilization. The vacuum source VS is operable to remove fluid from the inner cavity 43 of the first containment track 26 or otherwise near the first containment layer 32. The vacuum source VS can be a suction airflow provided from a vehicular system or can be vented to space.

Figure 6:
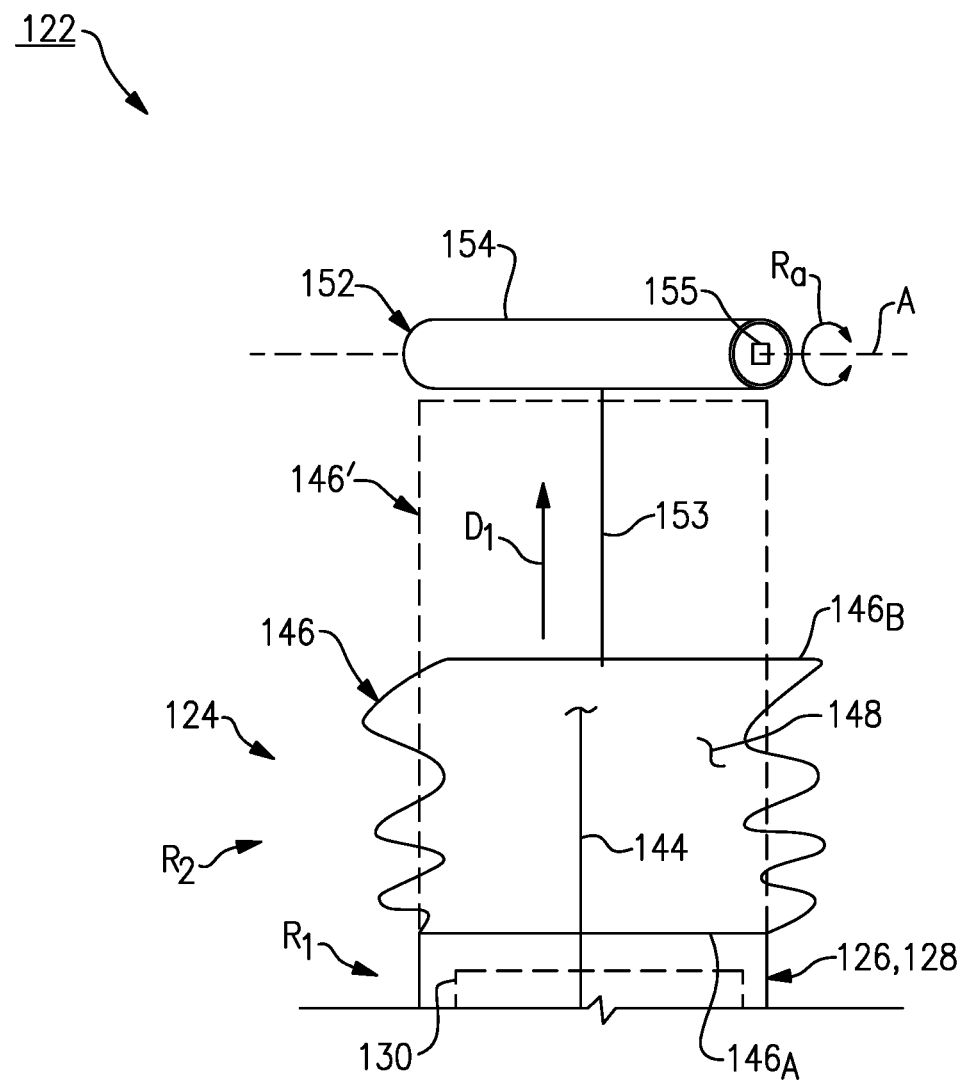
FIG. 6 illustrates a waste management system according to a second example.

FIG. 6 illustrates a waste management system 122 including a garment 124 according to a second example. Garment 124 can have features of the first and second regions R1, R2 of garment 24 shown in FIGS. 2-5, and therefore these features not discussed in further detail.

Garment 124 includes a collapsible storage container 146 coupled to actuation assembly 152 by at least one linkage 153. The linkage 153 can be one or more straps, and can be made of nylon webbing, for example. In the illustrated example, spool 154 is located external to storage cavity 148. The storage container 146 is expandable to a second position 146' such that drawing a second end 146B of the storage container 146 in direction D1 away from first end 146A of the storage container 146 causes a portion of cleansing member 144 to be drawn into storage cavity 148. In an alternative example, the actuation assembly 152 is omitted, and the storage container 146 can be manually collapsed or expanded.

Figure 7:
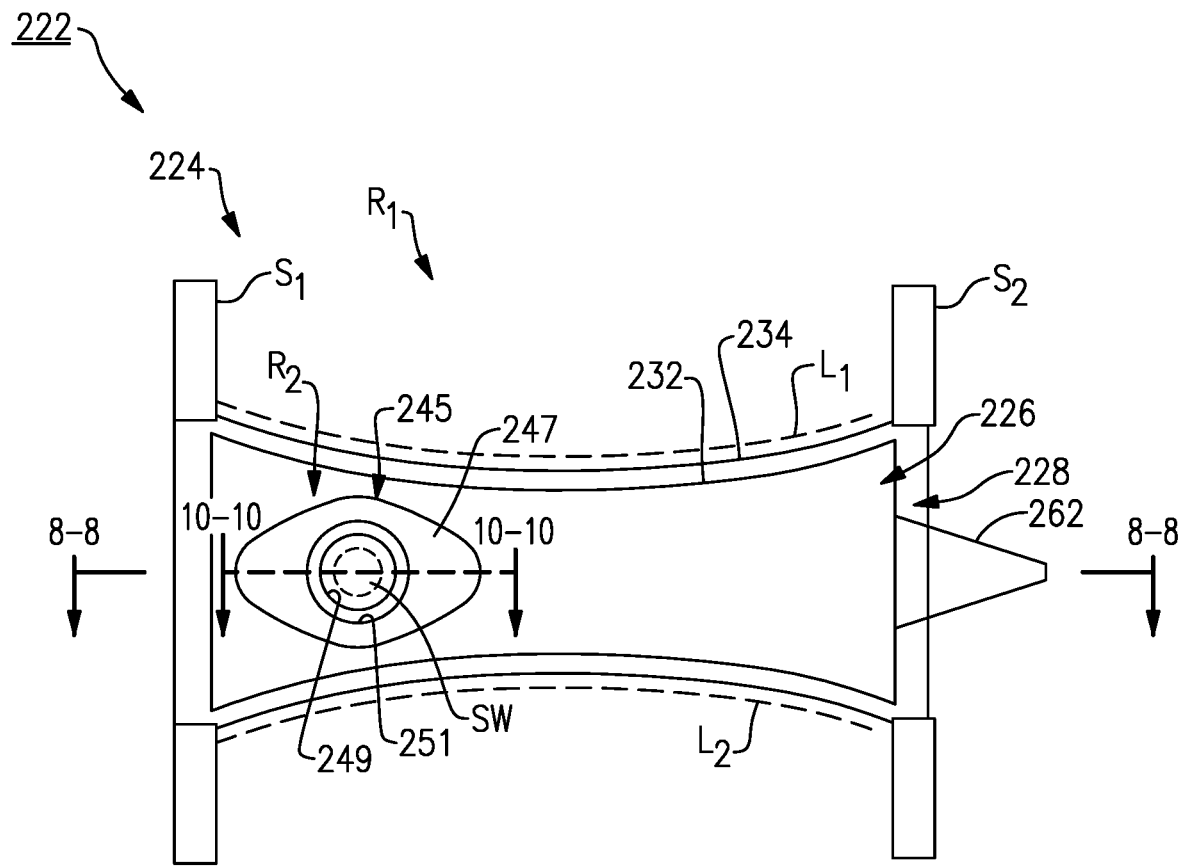
FIG. 7 illustrates a plan view of a waste management system according to a third example.
Figure 8:
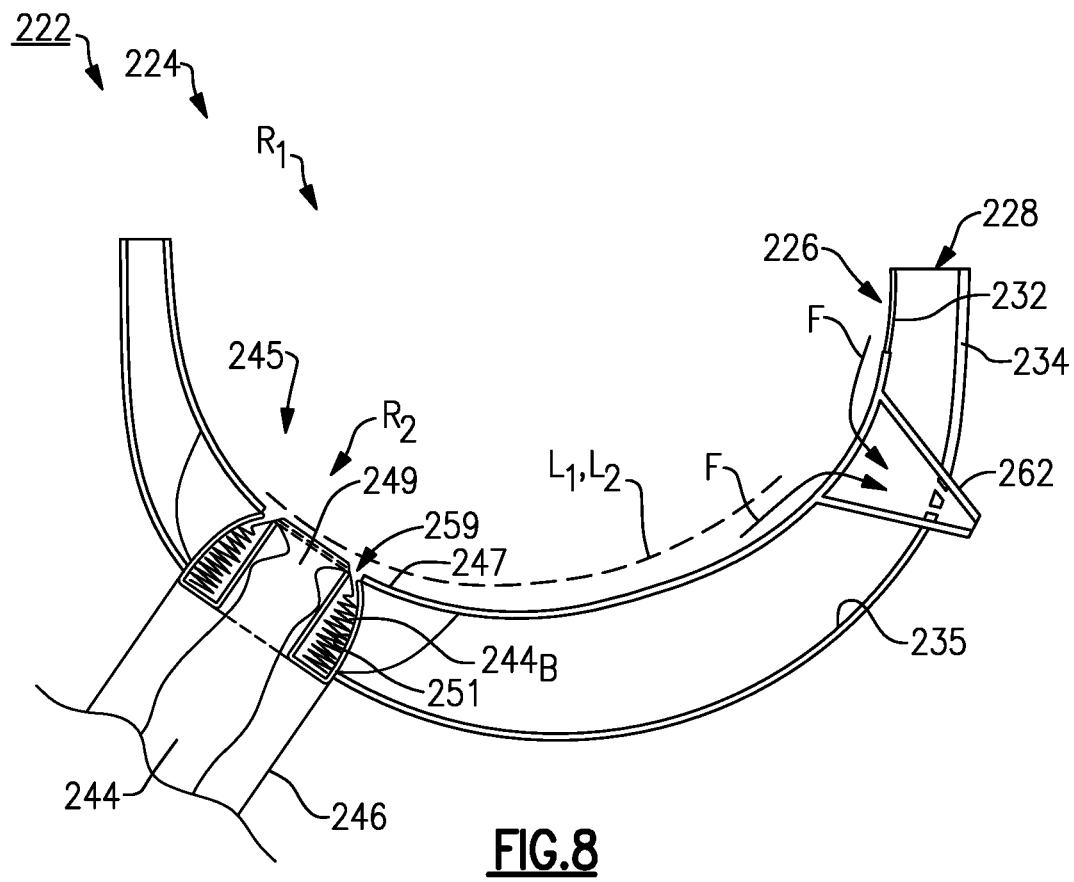
FIG. 8 is a sectional view of the waste management system of FIG. 7 along reference line 8-8.
Figure 9:
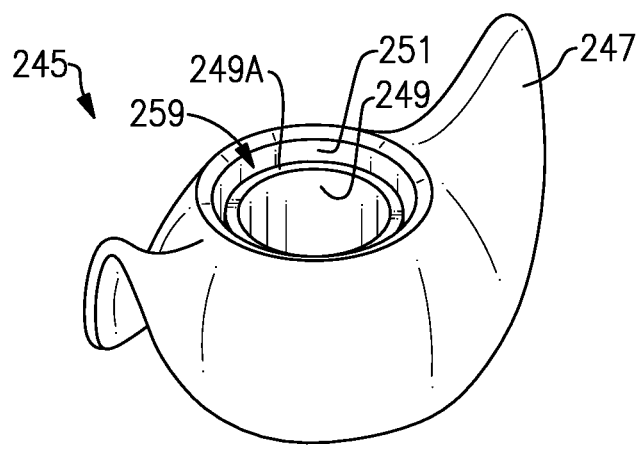
FIG. 9 is a perspective view of a containment interface for the waste management system of FIG. 7.

FIGS. 7-10 illustrate a waste management system 222 including a garment 224 according to a third example. In the illustrated example, the body side layer 30 of FIGS. 2 and 3 is optionally omitted, such that first containment layer 232 is configured for direct abutment with the person. Referring to FIGS. 7-9, the waste management system 222 includes a containment interface 245 situated for abutment near the anus of the person for removal of solid waste SW deposited adjacent to the first containment layer 232 when the garment 224 is worn. The containment interface 245 includes a generally flexible, elastic locator 247 having a contoured profile to seal against the skin and to bias the buttocks of the person away from each other and seal against the skin.

Figure 10:
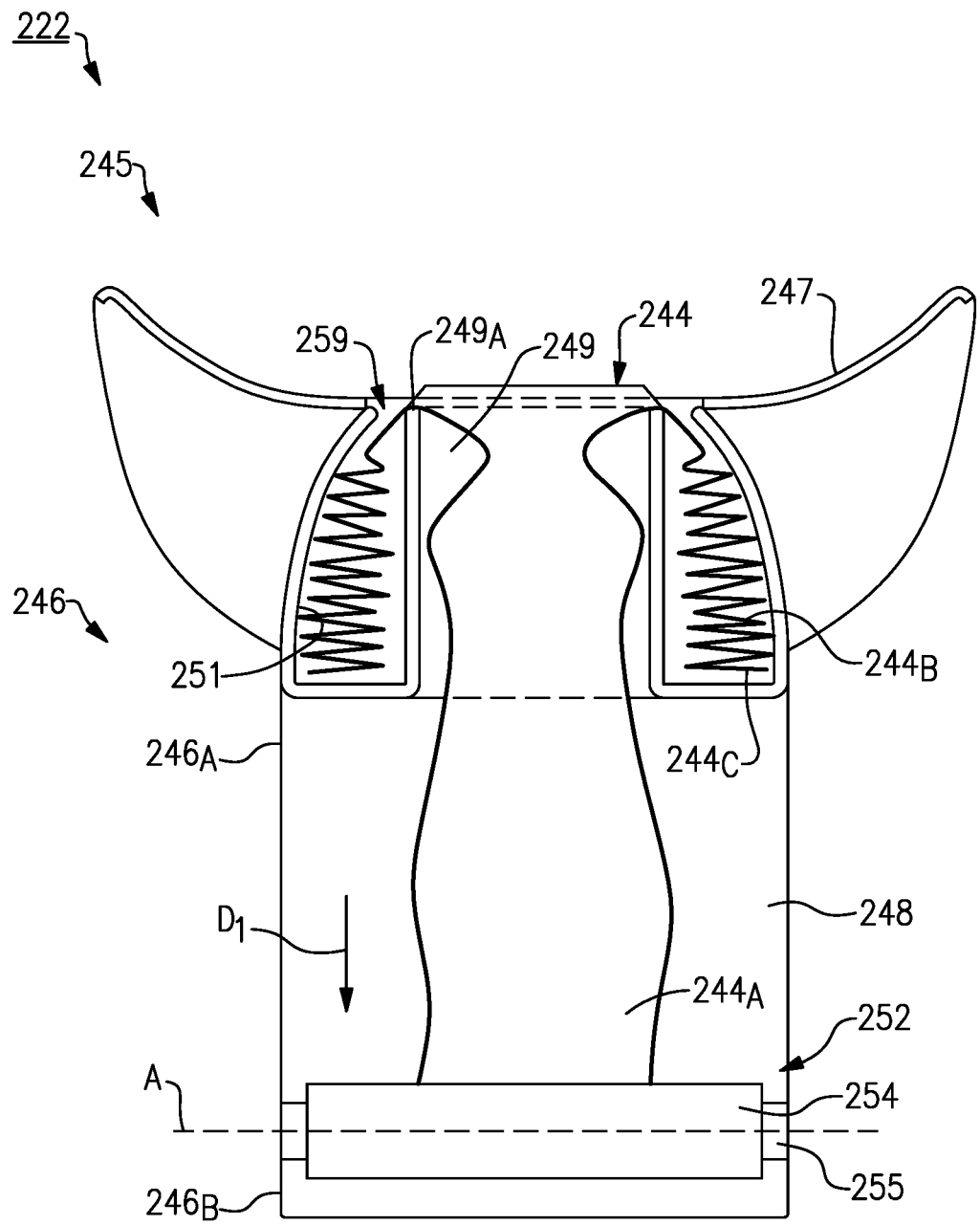
FIG. 10 is a sectional view of the containment interface along reference line 10-10 of FIG. 7.

Referring to FIG. 10, with continued reference to FIGS. 7-9, the containment interface 245 defines a waste passage 249 in communication with storage cavity 248 of storage container 246. The elastic locator 247 can serve to align the waste passage 249 with the anus. The containment interface 245 defines an annular feed cavity 251 for receiving a length 244B of cleansing member 244. Cleansing member 244 can have an elongated, tube-shaped geometry having an annular cross-section, for example. The cleansing member 244 can be routed and drawn through an annular opening 259 defined about a rim 249A of the waste passage 249 and into storage cavity 248 in response to rotation of spool 254 about axis A utilizing the various techniques disclosed herein. Translation of or movement of the cleansing member 244 relative to the first containment layer 232 causes removal of solid waste SW and cleansing of the adjacent skin adjacent to the containment interface 245.

Waste management system 22, 122, 222 functions as a single system for separation and removal of both urine and fecal matter. Prolonged contact of the waste with the body is reduced. This reduces a likelihood of irritation, rash, or infection occurring. Waste management system 22, 122, 222 effectively stores waste to reduce adverse health issues from occurring, and increases a likelihood of safe operation of the pressurized, protective suit 20 and safe operations completed by the user while inside of the pressurized suit 20. Garment 24, 124, 224 can be disposable or can be reusable with consumable items such as body side layer 30, 130 and cleansing member 44, 144, 244 for example.

Although the different examples have a specific component shown in the illustrations, embodiments of this disclosure are not limited to those particular combinations. It is possible to use some of the components or features from one of the examples in combination with features or components from another one of the examples. It should also be understood that any particular quantities disclosed in the examples herein are provided for illustrative purposes only.

Furthermore, the foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A waste management system for long duration vehicle operations comprising:
   a garment comprising:
      a first, substantially impermeable containment layer;
      a containment interface defining a passage;
      a storage container extending from the containment interface;
      a cleansing member routed through the passage, and into the storage container, the cleansing member moveable relative to the first containment layer to remove solid waste; and an actuation assembly moveable to draw a portion of the cleansing member into the storage container in response to activation of a control mounted to a protective suit.

2. The waste management system as recited in claim 1, comprising a body side layer extending along the first containment layer to define a first cavity, the body side layer including a coarse mesh fabric weave having a construct that allows passage of liquid waste into the first cavity, but obstructs passage of solid waste.

3. The waste management system as recited in claim 1, comprising a second, substantially impermeable containment layer extending along the first containment layer to define a second cavity, wherein a portion of the cleansing member is received in the second cavity.

4. The waste management system as recited in claim 1, wherein the storage container is expandable such that drawing an end of the storage container away from first containment layer causes a portion of the cleansing member to be drawn into a storage cavity defined by the storage container.

5. The waste management system as recited in claim 1, wherein the actuation assembly includes a spool coupled to the cleansing member, the spool mechanically attached to a torsion cable, and the control mechanically attached to the torsion cable.

6. The waste management system as recited in claim 1, comprising:
a capture funnel selectable coupled to a vacuum source operable to remove fluid near the first containment layer.

* * * * *